(12) United States Patent
Laty

(10) Patent No.: US 11,167,053 B1
(45) Date of Patent: Nov. 9, 2021

(54) ANTIVIRUS AND RADIATION DETECTION SYSTEM

(71) Applicant: Mark Laty, Miami, FL (US)

(72) Inventor: Mark Laty, Miami, FL (US)

( * ) Notice: Subject to any disclaimer, the term of this patent is extended or adjusted under 35 U.S.C. 154(b) by 0 days.

(21) Appl. No.: 17/206,775

(22) Filed: Mar. 19, 2021

Related U.S. Application Data

(60) Provisional application No. 63/016,755, filed on Apr. 28, 2020.

(51) Int. Cl.
*A61L 2/10* (2006.01)
*A41D 13/11* (2006.01)
*A61L 2/24* (2006.01)

(52) U.S. Cl.
CPC .............. *A61L 2/10* (2013.01); *A41D 13/11* (2013.01); *A61L 2/24* (2013.01); *A61L 2202/11* (2013.01); *A61L 2202/14* (2013.01); *A61L 2202/16* (2013.01)

(58) Field of Classification Search
None
See application file for complete search history.

(56) References Cited

U.S. PATENT DOCUMENTS

| 8,960,190 | B2* | 2/2015 | James | A61L 9/22 128/202.25 |
| 10,195,300 | B2* | 2/2019 | Lloyd | A61L 2/084 |
| 10,335,618 | B2* | 7/2019 | Zhou | A62B 18/02 |
| 2007/0101867 | A1* | 5/2007 | Hunter | A62B 11/00 96/224 |
| 2013/0340768 | A1* | 12/2013 | Gebrewold | B29C 45/14786 128/863 |
| 2017/0246329 | A1* | 8/2017 | Lloyd | A61L 2/10 |
| 2018/0311515 | A1* | 11/2018 | Wilson | A62B 18/08 |

FOREIGN PATENT DOCUMENTS

| AU | 2020100503 | | 5/2020 |
| CN | 205409781 U | * | 8/2016 |
| CN | 111632184 | | 9/2020 |
| CN | 211910628 | | 11/2020 |
| IN | 202021038802 | | 10/2020 |

* cited by examiner

*Primary Examiner* — Andrew Smyth

(74) *Attorney, Agent, or Firm* — The Concept Law Group, PA; Scott D. Smiley; Scott M. Garrett

(57) ABSTRACT

A system and method for an antivirus and radiation detection system configured to protect a wearer is provided. The system includes a personal protective equipment for preventing respiratory infection that includes a body configured to cover a nose and mouth of the user the body including at least one filter element disposed in the body that allows air to pass through the filter element from a first side of the body to a second side of the body; the filter element having a filter media; an ultraviolet light element disposed in the filter element that provides ultraviolet light into the filter media; and a pulsing laser element disposed in the filter element.

9 Claims, 6 Drawing Sheets

ANTIVIRUS AND RADIATION DETECTION SYSTEM

CROSS-REFERENCE TO RELATED APPLICATIONS

This application claims priority to U.S. Provisional Patent Application Ser. No. 63/016,755 which was filed Apr. 28, 2020, the entirety of which is hereby incorporated by reference.

FIELD OF THE INVENTION

The present invention relates generally to the field of personal protection systems, and more specifically to a system and method for an antivirus and radiation detection system configured to protect a wearer.

BACKGROUND OF THE INVENTION

Recently, wearing personal protective equipment (PPE) has become more common than ever before due to the rampant spread of infectious diseases and dangerous bacteria. As a result of this rampant spread, protective precautions such as frequent disinfecting of areas subject to exposure to multiple individuals has become the standard. For example, methods such as ultraviolet (UV) radiation, misting of disinfectants, and other applicable forms of physical sterilization are frequently applied to common spaces in order to reduce the amount of exposure to infectious disease particles. Although the aforementioned methods have become customary, additional protective measures are required in order to either ensure the safety of individuals frequenting these common spaces or prevent infected individuals from spreading illnesses to others. For example, despite the fact that PPE such as masks, face shields, googles, etc. have recently become typical within public spaces, the aforementioned only seek to prevent the user from coming into direct contact with infectious diseases and dangerous bacteria. The aforementioned PPE fails to include mechanisms that automatically sanitize the PPE itself along with the proximate surroundings of the PPE; therefore, potentially dangerous microorganisms that come into contact with the PPE persist on the surface of the PPE or invade components of the PPE increasing the risk of exposure of the user to the infectious diseases particles and/or dangerous bacteria.

Methods of sanitation such as ultraviolet light exposure, gamma radiation, sanitation agents (detergents, acids, disinfectants, etc.), and others are known to eradicate infectious diseases particles and/or dangerous bacteria in the air or on surfaces. However, direct exposure of the user to the aforementioned is extremely harmful due to the fact that they are biologically hazardous and may destroy living cells, produce gene mutations, and cause cancer.

Therefore, a need exists to overcome the problems with the prior art as discussed above. In particular, what is needed is a system to not only protect the user from direct contact with infectious diseases particles and/or dangerous bacteria, but also eradicate sources of infectious diseases particles and/or dangerous bacteria within proximity of the user in a safe manner in order to decrease probability of exposure to said infectious diseases particles and/or dangerous bacteria altogether.

SUMMARY OF THE INVENTION

The invention provides an antivirus and radiation detection system that overcomes the hereinafore-mentioned disadvantages of heretofore-known personal protective equipment. More particularly, the invention provides a personal protective equipment for preventing respiratory infection that includes a body configured to cover a nose and mouth of the user the body including at least one filter element disposed in the body that allows air to pass through the filter element from a first side of the body to a second side of the body; the filter element having a filter media; an ultraviolet light element disposed in the filter element that provides ultraviolet light into the filter media; and a pulsing laser element disposed in the filter element. In some embodiments, the personal protective equipment includes at least a processor, a power source coupled to the processor, a motion detection sensor, and an image sensor; wherein the power source, ultraviolet light element, pulsing laser element, motion detection sensor, and image sensor are communicatively coupled to the processor. In some embodiments, the body further includes a ventilation mechanism including a plurality of fans coupled to a ventilation power source. In some embodiments, the body further includes a plurality of breathing valves; wherein the ultraviolet light element is integrated along a first exterior surface associated with a first breathing valve and the pulsing laser element is integrated along a second exterior surface associated with a second breathing valve.

In some embodiments, the personal protective equipment is an antivirus face apparatus including a motherboard including a top surface and a bottom surface; a planar surface comprising a left temple disposed on a leftmost side and a right temple disposed on a rightmost side wherein the planar surface continuously extends vertically from the top surface to the bottom surface; wherein the motherboard includes; at least a processor; and a power source coupled to the processor. In some embodiments, the antivirus face apparatus includes a motion detection sensor; an ultraviolet light element; and an image sensor; wherein the power source, ultraviolet light element, pulsing laser element, motion detection sensor, and image sensor are communicatively coupled to the processor.

In some embodiments, the personal protective equipment is an antivirus apparatus including an eyewear frame configured to be integrated with a face shield. The eyewear frame including at least a processor; a power source coupled to the processor; an ultraviolet light element; and a pulsing laser element; wherein the ultraviolet light element and pulsing laser element are communicatively coupled to the processor. In some embodiments, the antivirus apparatus further includes a motion detection sensor; an image sensor; and a ventilation mechanism including a plurality of fans coupled to a ventilation power source; wherein the ventilation mechanism is configured to be integrated into the eyewear frame and generate an airflow away from the eyewear frame. In some embodiments, the eyewear frame include a plurality of frame holders configured to function as receptacles for at least one lens configured for ultraviolet A (UVA), ultraviolet B (UVB), ultraviolet C (UVC), or any other applicable form of radiation.

In some embodiments, the motion detection sensor is configured to detect a plurality of motion activity data within a predefined proximity of the personal protective equipment; wherein based on the plurality of motion activity data, the processor is configured to activate the ultraviolet light element to radiate ultraviolet light waves. In some embodiment, the pulsing laser element includes a scintillator designed and configured to emit a plurality of low-energy photons based on the plurality of motion activity data.

In some embodiments, the personal protective equipment includes a body temperature sensor communicatively coupled to the processor and a short-range wireless communication mechanism configured to communicate with the processor to generate a personal area network (PAN).

Although the invention is illustrated and described herein as embodied in a cosmetic material applicator, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the installation tool. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1A:
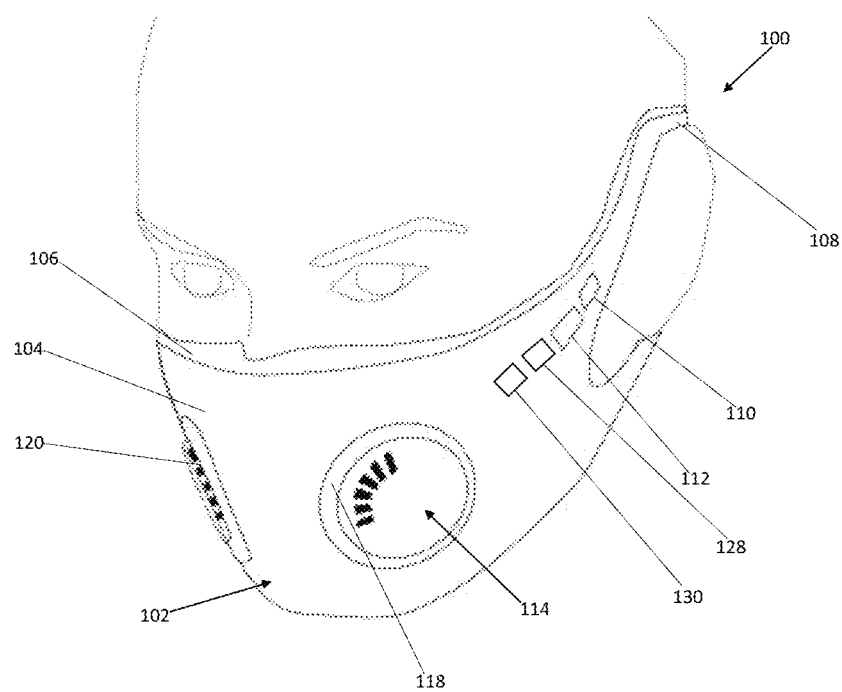
FIGS. 1A-1B are perspective views of an exemplary face mask including an antivirus and radiation detection system, according to an example embodiment.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

Figure 1B:
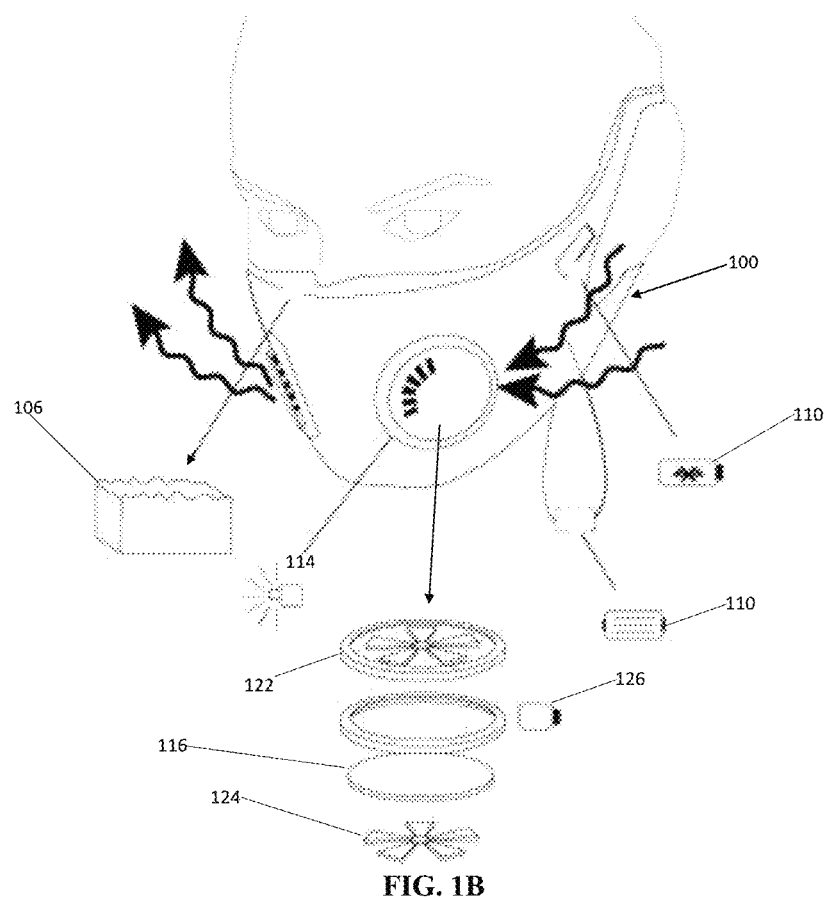

Referring now to FIGS. 1A-1B, a personal protective equipment 100 (PPE) is depicted, according to an example embodiment. In some embodiments, PPE 100 is a mask; however, PPE 100 may also include equipment that is worn by the user such as but not limited to eyewear (goggles, glasses, etc.), a visor, face shield, clothing (gloves, apparel, etc.), and/or any other applicable wearable. In some embodiments, PPE 100 includes a mask body 102 including an upper exterior surface 104; wherein a comfort layer 106 is allocated along upper exterior surface 104. PPE 100 further includes a temple mechanism 108, at least a processor 110, a power source 112 configured to be coupled to processor 110, a filter element 114 (breathing valve) configured to include a filter media 116, an ultraviolet light element 118 configured to be communicatively coupled to processor 110, a laser pulsing element 120 configured to be communicatively coupled to processor 110, a ventilation mechanism 122 including a plurality of fans 124, a camera 126, a motion detector sensor 128 configured to be communicatively coupled to processor 110, and a body temperature sensor 130 configured to be communicatively coupled to processor 110. PPE 100 may be formed from a single piece or from several individual pieces joined or coupled together. It is to be understood that PPE 100, along with components of PPE 100, may be composed of one or more wovens, carbon steel, stainless steel, aluminum, titanium, composites, ceramics, polymeric materials such as polycarbonates, such as acrylonitrile butadiene styrene (ABS plastic), Lexan™, Makrolon™, or any other applicable material configured to prevent direct exposure of infectious diseases particles and/or dangerous bacteria to the user. PPE 100 and all of its components may be manufactured from a variety of different processes including an extrusion process, a mold, welding, shearing, punching welding, folding etc.

In some embodiments, as depicted in FIG. 1, upper exterior surface 104 may be allocated directly beneath the eyes of the user allowing PPE 100 to be donned in a manner that simultaneously encloses the mouth and nose area of the user while allowing the user to have uninterrupted visibility from directly above upper exterior surface 104. In some embodiments, comfort layer 106 may be disposed along upper exterior surface 104 in order to ensure that upper exterior surface 104 does not itch and/or irritate the skin or eyes of the user. Examples of materials included in comfort layer 106 include but is not limited to polyurethane, wovens, non-wovens, drawn-loop knits, down and feather, synthetic fibers, latex foam, organic wool, or any other applicable material configured to provide comfort to the user. In some embodiments, comfort layer 106 is composed of polyurethane having a plurality of capillaries configured to retain breathability. Temple mechanism 108 is configured to serve as the point of affixing PPE 100 to the user at and/or proximate to the temple area of the user and in some instances a portion of the ears of the user as well. In some embodiments, temple mechanism 108 may be a temple headband, an ear-contacting loop, or any other applicable mechanism configured to retain placement of PPE 100 on the mouth and nose area of the user. It is to be understood that temple mechanism 108 may be a left and right side temple contacting mechanism configured to be in direct contact and/or proximate to the ears of the user, wherein the temple mechanism 108 may span the at least a portion of the back of the head of the user or contact at least a portion of the ears of the user in order to securely retain PPE 100 to the face.

In some embodiments, mask body 102 may be shaped and sized as a receptacle, planar surface, or any other applicable type of structure configured to efficiently enclose the mouth and nose area of the user in order to prevent expose to infectious diseases particles and/or dangerous bacteria. In some embodiments, mask body 102 may be multi-layered with layers such as but not limited to a filter layer, a supportive layer, respirators, or any other applicable mask layers known to those of ordinary skill in the art. In some embodiments, mask body 102 is designed and configured to support attaching of components such as but not limited to breathing valves, filters, or any other applicable affixable components to an exterior surface of mask body 102. It is to be understood that mask body 102 is designed and configured to allow air to pass from an exterior surface of mask body 102 through filter element 114 to an interior surface of mask body 102 allowing the intruding air to come into contact with filter media 116.

In some embodiments, processor 110 is configured to execute memory storing instructions configured to activate one or more of ultraviolet light element 118, laser pulsing element 120, ventilation system 122, camera 126, motion detector sensor 128, and/or body temperature sensor 130. In some embodiments, PPE 100 is further configured to include an air quality sensor configured to be communicatively coupled to processor 110 allowing PPE 100 to detect the quality of air surrounding PPE 100 by presenting data transmitted by processor 110 to a display device. It is to be understood that processor 110 is designed and configured to function as a communication component to facilitate wireless communication between PPE 100 and its components along with other devices. For example, data collected by the air quality sensor is configured to include date, time, and air quality reading that is transmitted to processor 110, wherein processor 110 is configured to transmit the collected data to a computing device such as but not limited to a laptop computer, a tablet computer, a smartphone, a desktop computer, a Personal Digital Assistant (PDA), a wearable device, or any other applicable device configured to support wireless communications.

In some embodiments, mask body 102 further includes a short-range wireless communication mechanism 132 configured to generate a personal area network (PAN), and is communicatively coupled to processor 110. Examples of PANs includes but is not limited to Bluetooth, NFC, Zigbee, Ultra Wide Band (UWB), infrared, WLAN 802.11, or any other applicable mechanism for generating PANs known to those of ordinary skill in the art. In some embodiments, data collect by processor 110 from the applicable components (sensors) of PPE 100 is configured to be transmitted to the computing device over a network (not shown) wherein the network is configured to be a wireless local area network (WLAN), wireless personal area network (WPAN), wireless wide are network (WWAN), universal mobile telecommunications service (UMTS), enhanced packet system (EPS), new radio wireless network (NR), internet, LTE, GSM, WCDMA, $3^{rd}$ generation partnership project (3GPP), a combination of more than one network and/or more than one type of network, or any other applicable communications network known to those of ordinary skill in the art. In some embodiments, power source 112 may be any form of battery (in some instances rechargeable), supercapacitor, ultracapacitors, solar cells (configured to power electrical circuitry of PPE 100), or any other applicable power source known to those of ordinary skill in the art. In some embodiments, power source 112 is a combination of a capacitor and a rechargeable battery retained in at least one housing. It is to be understood that power source 112 is configured to be allocated anywhere on PPE 100 that allows applicable components of PPE 100 to be efficiently activated. For example, power source 112 may be disposed on and/or proximate to temple mechanism 108 in a manner in which power source 112 securely hangs from temple mechanism 108 in a visible manner or power source 112 may be securely concealed from visibility within mask body 102 cloaked by at least one of the multiple layers of mask body 102. In some embodiments, power source 112 is configured to be charged via a power receiving port allocated at and/or proximate to power source 12 or mask body 102. Examples of a power receiving port include but is not limited to USB A, USB B, USB Micro A, USB Micro B, USB Mini A, USB Mini B, or any other applicable mechanism configured to enable reception of electrical energy in order to charge power source 112.

In some embodiments, camera 126 is designed and configured to include a thermal scanning component, a blacklight component, or any other applicable type of imaging technology known to those of ordinary skill in the art configured to detect potential infectious diseases particles and/or dangerous bacteria. In some embodiments, data collect by camera 126 is transmitted to a display device via processor 110 over the network for presentation purposes.

In some embodiments, filter element 114 is configured to permit air to pass from the exterior surface of mask body 102 through to an interior surface of mask body 102, wherein filter element 114 is designed to include an interior chamber shaped and sized to house filter media 116. It is to be understood that filter media 116 serves as a chamber within mask body 102 configured to collect contaminants being filtered from the air entering filter element 114 in order to prevent said contaminants from entering the interior surface of mask body 102. In some embodiments, filter media 116 is configured to be interchangeable and in some instances detached from filter element 114 for cleaning purposes when PPE 100 is not donned by the user. It is to be understood that upper exterior surface 104 is an area of mask body 102 that is distanced from a plane that bisects filter element 114 configured to be positioned near at least one cheek and/or jaw area of the user when PPE 100 is donned. It is to be understood that ultraviolet light element 118 is configured to be positioned proximate to and/or within filter element 114 allowing ultraviolet light element 118 to emit UV rays into filter media 116 eradicating the contaminants within filter media 116; and in some embodiments, ultraviolet light element 118 further includes a UV detector component configured to detect if there is a wavelength longer than a predetermined wavelength threshold in order for processor 110 to determine if ultraviolet light element 118 needs to sanitize filter element 114 and/or the detect presence of infectious diseases particles and/or dangerous bacteria. It is to be understood that ultraviolet light element 118 is designed and configured to radiate UVC 220 nm light waves or less subject to the configuration of PPE 100 based upon the presence of bacteria within or near filter element 114 and/or filter media 116. In some embodiments, ultraviolet light element 118 is configured to emit the UVC to both filter media 116 and to the surrounding environment of PPE 100 outside of mask body 102, wherein processor 110 communicates with motion detector sensor 128 and based on motion detector sensor 128 detecting a plurality of motion activity within a predefined proximity from PPE 100, and camera 126 scans for infectious diseases particles and/or dangerous bacteria within six feet of PPE 100, processor 110 instructs ultraviolet light element 118 to emit in an outward direction of mask body 102 (through filter element 114 or other light emitting surface) into the areas camera 126 and motion detector sensor 128 has detected the infectious diseases particles and/or dangerous bacteria to be present in. Emitting of UVC from ultraviolet light element 118 is subject to a plurality of factors such as but not limited to battery capacity of power source 112, distance of infectious diseases particles and/or dangerous bacteria from motion detector sensor 128, and any other applicable power-related, distance-related, and/or capacity related factors.

In some embodiments, ventilation mechanism 122 is a system configured to generate air circulation patterns via plurality of fans 124 preventing air containing infectious diseases particles and/or dangerous bacteria proximate to filter element 114 and/or mask body 102 from entering the internal surface of mask body 102. It is to be understood that ventilation mechanism 122 may include a power source of its own included in PPE 100 configured to power plurality of fans 124 and/or ventilation mechanism 122 may draw power from power source 112 allowing ventilation mechanism 122 to be distributed to plurality of fans 124 accordingly. In some embodiments, ultraviolet light element 118 and/or laser pulsing element 120 are configured to include a light emitting mechanism, such as a LED, configured to be allocated on mask body 102 in an external manner in which the light emitting mechanism is configured to at least partially encircle filter element 114 and/or filter media 116 allowing the light emitting mechanism to externally emit a plurality of colors based on the function ultraviolet light element 118 and/or laser pulsing element 120 is performing while simultaneously being proximate to filter element 114 and/or filter media 116. For example, the light emitting element may continuously emit blue when in a standby mode (ultraviolet light element 118 and/or laser pulsing element 120 is not emitting) and red when in an active mode (ultraviolet light element 118 and/or laser pulsing element 120 is emitting on filter element 114 and/or filter media 116), wherein the light emitting element may be powered by power source 112. In some embodiments, ventilation mechanism 122 may be a fan-les or passive ventilation system configured to function as a unidirectional air valve for distributing gusts to drive bacteria away from mask body 102.

It is to be understood that laser pulsing element 120 is configured to be positioned on a surface laterally opposing ultraviolet light element 118 allowing ultraviolet light element 118 to emit from its designated side and laser pulsing element 120 to emit from the laterally opposing side. In some embodiments, laser pulsing element 120 is a mechanism configured to emit ultrashort pulses of light such as but not limited to femtosecond laser, gamma rays, electron beams, x-rays, y-rays, or any other applicable high-energy electrons. It is to be understood that femtosecond lasers emitted by laser pulsing element 120 may be configured to sanitize filter element 114 and/or filter media 116. In some embodiments, laser pulsing element 120 utilizes a scintillator to assist in emitting light. In some embodiments, laser pulsing element 120 is configured to include a radioactive particles detection mechanism, such as a scanning sensor, designed to detect gamma rays, energetic particles, and/or scan for infectious particles within 6 feet of camera 126 and/or motion detector sensor 128, wherein motion detector sensor 128 transmits data associated with the detected gamma rays and/or energetic particles to processor 110 allowing processor 110 to transmit instructions to laser pulsing element 120 to sanitize/disinfect by emitting femtosecond lasers into the environment associated with PPE 100 including contaminants requiring sanitation. It is to be understood that the radioactive particles detection mechanism may be a separate component from laser pulsing element 120 configured to be communicatively coupled to processor 110. In some embodiments, one or more fans of plurality of fans 124 may be activated by processor 110 based on laser pulsing element 120 collecting data indicating presence of infectious particles within the vicinity of PPE 100. The collected data is transmitted to processor 110 in which processor 110 may determine which applicable fan of plurality of fans 124 to activate. For example, data collected by laser pulsing element 120 may indicate that laser pulsing element 120 detects infectious diseases particles and/or dangerous bacteria approaching filter element 114 from a particular direction in which processor 110 may activate a fan of plurality of fans 124 configured to generate an air circulation pattern in the direction preventing the approaching infectious diseases particles and/or dangerous bacteria from entering the interior surface of mask body 102.

Figure 2:
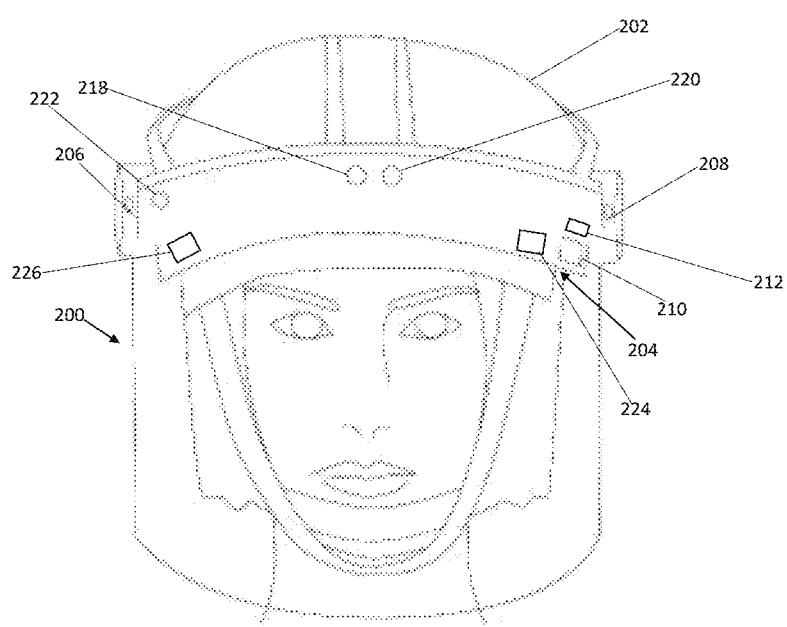
FIG. 2 is a perspective view of an exemplary face shield including the antivirus and radiation detection system, according to an example embodiment.

Referring now to FIG. 2, a face shield 200 is depicted, according to an example embodiment. It is to be understood that face shield 200 may be affixable to applicable personal protective equipment donned by the user such as a helmet 202, as illustrated in FIG. 2. However, a temple mechanism 204 may serve as visor/headband allowing face shield 200 to be attached and/or integrated into temple mechanism 204 and extend from a top portion of the face of the user (proximate to the hairline and/or forehead) vertically in a continuous manner up to below the chin area of the user, wherein face shield 200 is a planar surface configured to be in direct contact with a portion of the user. In some embodiments, face shield 200 is transparent, tinted, mirrored, and/or configured to permit the user to view chemically activated and/or photoactivated substances, and face shield 200 is designed to support various shapes and curves subject to the applicable configuration. In some embodiments, face shield 200 may be designed to rest on the nose of the user and/or a pair of glasses the user is wearing if applicable. It is to be understood that the purpose of face shield 200 is to ensure that the mouth and nose area of the user is substantially enclosed, wherein access to the mouth and nose area is only possible through an opening allocated at the bottommost point of face shield 200 extending horizontally from a leftmost side of temple mechanism 204 to a rightmost side of temple mechanism 208. In some embodiments, face shield 200 may be integrated into a leftmost side 206 of face shield 200 to a rightmost side 208 of face shield 200. Sides 206 and 208 may be configured to include a hinge or other applicable pivoting mechanism to ensure that face shield 200 may be moved upward along the hinge resulting in face shield 200 transitioning from a vertical orientation to a horizontal orientation upon application of an upward force to face shield 200 from the user.

In some embodiments, temple mechanism 204 may function as a motherboard-like mechanism designed and configured to include a processor 210, a power source 212, an ultraviolet light element 218, a laser pulsing element 220, a motion detector sensor 222, and a camera 224. Processor 210 is designed and configured to be communicatively coupled to power source 212, ultraviolet light element 218, laser pulsing element 220, motion detector sensor 222, and camera 224; wherein processor 210 is configured to execute memory storing instructions configured to activate one or more of ultraviolet light element 218, laser pulsing element 220, motion detector sensor 222, or camera 224. In some embodiments, temple mechanism 204 further includes a short-range wireless communication mechanism 226 configured to communicate with processor 210 and generate a personal area network. In some embodiments, camera 224 includes a thermal scanning component and laser pulsing element 220 includes one or more electrical components configured to support detection of radiation within the vicinity of motion detector sensor 222. In some embodiments, data collected by laser pulsing element 220 and camera 224 is transmitted to processor 210, wherein processor 210 may transmit the collected data over an applicable network to a display device configured to produce a visual output. It is to be understood that face shield 200 is designed and configured to prevent the user from direct exposure to infectious diseases particles and/or dangerous bacteria by simultaneously serving as a barrier from particles in the environment and detect and subsequently eradicate particles in the direct view of laser pulsing element 220, motion detector sensor 222, and/or camera 224. In some embodiments, temple mechanism 204 further includes a body temperature sensor configured to detect the internal body temperature of individuals detected by camera 224.

Figure 3:
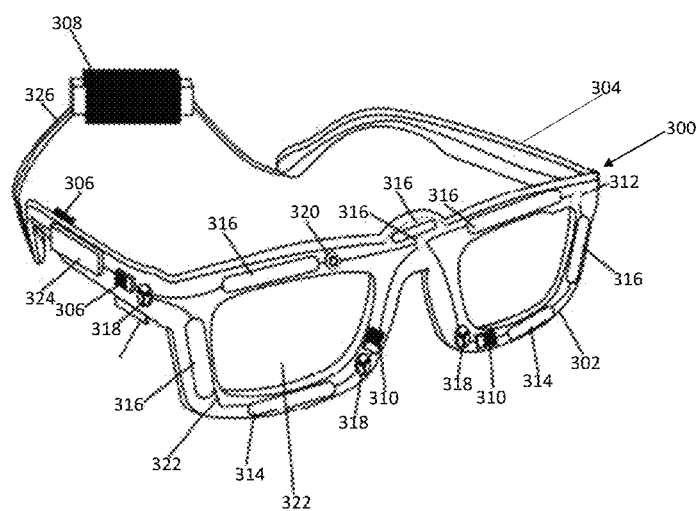
FIG. 3 is a perspective view of an exemplary eyewear including the antivirus and radiation detection system, according to an example embodiment.

Referring now to FIG. 3, an eyewear 300 is depicted, according to an example embodiment. In some embodiments, eyewear 300 includes a frame 302, a temple mechanism 304, a processor 306, a power source 308, a motion detection sensor 310, at least a sensor 312, a pulsing laser element 314, an ultraviolet light element 316, a ventilation system 318, and a camera 320. In some embodiments, frame 302 includes a plurality of lens receptacles 322 shaped and sized to support retention of a variety of lens types including but not limited to UVA, UVB, UVC, polarized, or any other applicable type of lens. It is to be understood that eyewear 300 is designed and configured to be integrated into a face shield, such as face shield 200, wherein rather than components being allocated on helmet 202 they are allocated on eyewear 300, and eyewear 300 is integrated into the face shield allowing the face shield to be detachably affixed to eyewear 300 and be positioned in front of eyewear 300 in a manner that prevents the face shield from coming into direct contact with lenses of eyewear 300 along with the nose and mouth of the user ensuring that the face of the user is protected from exposure to bacteria and/or applicable airborne particles. U.S. Pat. No. 5,471,679 (Paoluccio, 1995) describes an exemplary configuration for an eyewear integrated with a face shield. In some embodiments, frame 302 further includes a short-range wireless communication mechanism 324. It is to be understood that sensor 312 may include a gyroscope, accelerometer, infrared sensor, proximity sensor, position sensor, biological data sensor, pressure sensor, vision/imaging sensor, measurement device, microphone, transducer, capacitance switch, pressure switch, scanner, gas/chemical detector, temperature sensor, radiation sensor, photoelectric sensor, particle sensor, motion sensor, leak sensor, humidity sensor, air quality sensor, semiconductor measurer, air quality sensor, wind speed sensor or any other applicable sensor (or combination thereof) configured to collect data known to those of ordinary skill in the art.

In some embodiments, temple mechanism 304 is designed and configured to horizontally extend from the temple area of the user to at least the back of the ears of the user, wherein a left temple tip and right temple tip come into direct contact with a portion of the ears of the user. In some embodiments, temple mechanism 304 includes a band/strap mechanism 326 configured to span the back of the head of the user and be affixed to left temple tip and right temple tip. In some embodiments, power source 308 and applicable associated wiring may be allocated within band/strap mechanism 326 wherein power source 308 may be covered or padded in order to increase comfort when donned by the user. In some embodiments, applicable toggles and buttons associated with power source 308, sensor 312, short-range wireless communication mechanism, or any other applicable component of eyewear 300 may be allocated along an exterior surface of frame 302 allowing the user to control the powering of applicable functions of eyewear 300.

Figure 4:
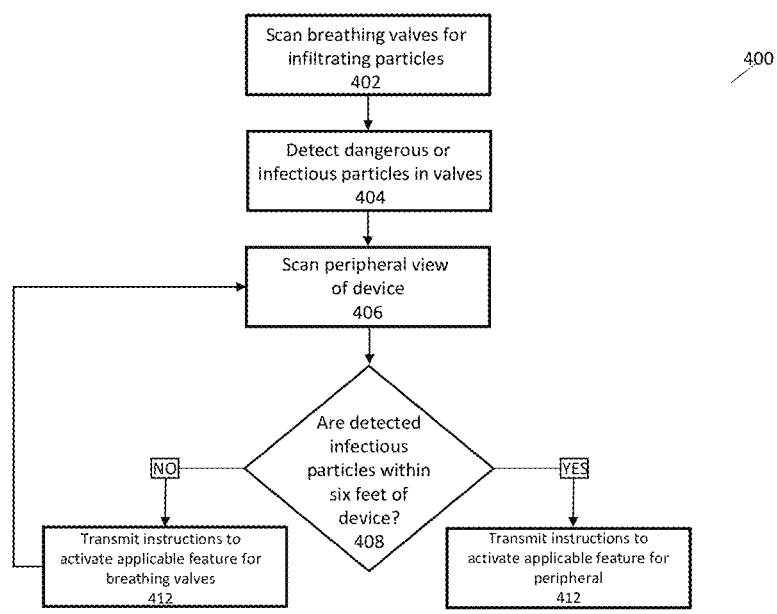
FIG. 4 is a block diagram illustrating an exemplary method for antivirus and radiation detection, according to an example embodiment.

Referring now to FIG. 4, an exemplary method of antivirus and radiation detection 400 is depicted, according to an example embodiment. It is to be understood that the undermentioned steps are bound to no particular order due to the fact that it is assumed for example purposes that when PPE 100, face shield 200, and eyewear 300 are powered on, processors 110, 210, & 306 are continuously transmitting data collected from at least one of the aforementioned sensors/components. It is to be further understood that while the undermentioned steps are being performed, air particles are continuously being filtered by filter element 114 in order to provide clean air to the interior side of mask body 102. At step 402, processor 110 instructs ultraviolet light element 118 and/or laser pulsing element 120 to scan one or more filter element 114 in order for processor 110 to determine whether the predetermined wavelength threshold has been exceeded and/or there is a presence of particle within filter element 114 and/or filter media 116, wherein ultraviolet light element 118 and/or laser pulsing element 120 comprehensively scans one or more filter element 114 for infectious particles. In some embodiments, camera 126 is configured to detect particles within filter element 114 alone and/or in combination with the utilization of a cascade impactor, optical particle counter (OPC), wide range aerosol spectrometer, aerodynamic particle sizer (APS), scanning mobility particle sizer (SMPS), or any other particle analyzer configured to be communicatively coupled to processor 110 and/or a computing device associated with processor 110. At step 404, ultraviolet light element 118 and/or laser pulsing element 120 transmits the collected particles data associated with filter element 114 and/or filter media 116 to processor 110 allowing processor 110 to determine particles are present within filter element 114 and/or filter media 116. At step 406, camera 126 and/or motion detector sensor 128 or a combination thereof scan the peripheral view of the user within no more than a six feet distance from camera 126 and/or motion detector sensor 128 for infectious particles that are either airborne or resting on a surface. In addition, camera 126 utilizes the thermal scanning component in order to detect abnormally high body temperature of objects captured by camera 126 and motion detector sensor 128. At step 408, processor 110 determines if the detected infectious particles within the peripheral view of PPE 100 are within six feet of PPE 100. If not, step 410 is occurs in which processor 110 instructs ultraviolet light element 118 and/or laser pulsing element 120 to emit applicable radiation sanitizing directly onto filter element 114 and/or filter media 116. Otherwise, step 412 occurs in which processor 110 instructs ultraviolet light element 118 and/or laser pulsing element 120 to emit applicable radiation toward the exterior of PPE 100 sanitizing infectious particles within the peripheral view. In some embodiments, sanitation of peripheral view and filter element 114 and/or filter media 116 via ultraviolet light element 118 and/or laser pulsing element 120 may be accomplished simultaneously.

Figure 5:
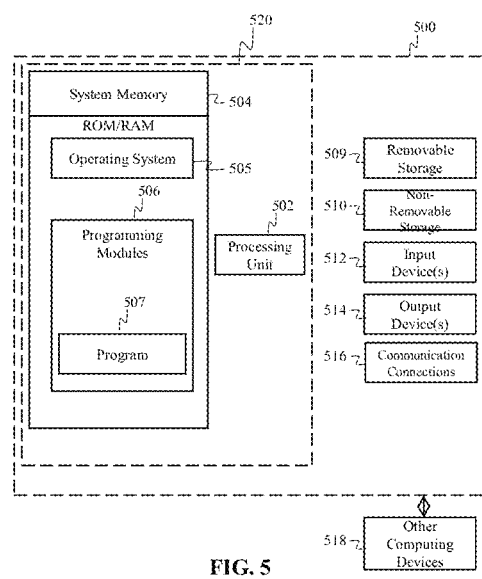
FIG. 5 illustrates a computer system according to exemplary embodiments of the present technology.

FIG. 5 is a block diagram of a system including an example computing device 500 and other computing devices. Consistent with the embodiments described herein, the aforementioned actions performed by processors 110, 210, & 306 may be implemented in a computing device (preferably a microprocessor), such as the computing device 500 of FIG. 5. Any suitable combination of hardware, software, or firmware may be used to implement the computing device 500. The aforementioned system, device, and processors are examples and other systems, devices, and processors may comprise the aforementioned computing device. Furthermore, computing device 500 may comprise an operating environment for PPE 100 and process/method 400. Process 400, and data related to said process may operate in other environments and are not limited to computing device 500.

With reference to FIG. 5, a system consistent with an embodiment of the invention may include a plurality of computing devices, such as computing device 500. In a basic configuration, computing device 500 may include at least one processing unit 502 and a system memory 504. Depending on the configuration and type of computing device, system memory 504 may comprise, but is not limited to, volatile (e.g. random access memory (RANI)), non-volatile (e.g. read-only memory (ROM)), flash memory, or any combination or memory. System memory 504 may include operating system 505, and one or more programming modules 506. Operating system 505, for example, may be suitable for controlling computing device 500's operation. In some embodiments, programming modules 506 may include, for example, a program module 507 for executing the actions of processors 110, 210, & 306, for example. Furthermore, embodiments of the invention may be practiced in conjunction with a graphics library, other operating systems, or any other application program and is not limited to any particular application or system. This basic configuration is illustrated in FIG. 5 by those components within a dashed line 520.

Computing device 500 may have additional features or functionality. For example, computing device 500 may also include additional data storage devices (removable and/or non-removable) such as, for example, magnetic disks, optical disks, or tape. Such additional storage is illustrated in FIG. 5 by a removable storage 509 and a non-removable storage 510. Computer storage media may include volatile and nonvolatile, removable and non-removable media implemented in any method or technology for storage of information, such as computer readable instructions, data structures, program modules, or other data. System memory 504, removable storage 509, and non-removable storage 510 are all computer storage media examples (i.e. memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 500. Any such computer storage media may be part of device 500. Computing device 500 may also have input device(s) 512 such as a keyboard, a mouse, a pen, a sound input device, a camera, a touch input device, etc. Output device(s) 514 such as a display, speakers, a printer, etc. may also be included. The aforementioned devices are only examples, and other devices may be added or substituted.

Computing device 500 may also contain a communication connection 516 that may allow device 500 to communicate with other computing devices 518, such as over a network in a distributed computing environment, for example, an intranet or the Internet. Communication connection 516 is one example of communication media. Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media.

The term computer readable media as used herein may include both computer storage media and communication media.

As stated above, a number of program modules and data files may be stored in system memory 504, including operating system 505. While executing on processing unit 502, programming modules 506 (e.g. program module 507) may perform processes including, for example, one or more of the stages of the process 400 as described above. The aforementioned processes are examples, and processing unit 502 may perform other processes. Other programming modules that may be used in accordance with embodiments of the present invention may include electronic mail and contacts applications, sensor data processing applications, word processing applications, spreadsheet applications, database applications, slide presentation applications, drawing or computer-aided application programs, etc.

What is claimed is:

1. A face mask preventing respiratory infection comprising:
    a mask body configured to cover a nose and mouth of a user, the mask body comprising:
        at least one filter element disposed in the mask body that allows air to pass through the filter element from a first side of the mask body to a second side of the mask body, the filter element having a filter media;
        an ultraviolet light element disposed in the filter element that provides ultraviolet light into the filter media; and
        a pulsing laser element disposed in the filter element.
2. The face mask of claim 1, further comprising at least a processor and a power source.
3. The face mask of claim 1, further comprising an image sensor.
4. The face mask of claim 2, further comprising a body temperature sensor configured to be communicatively coupled to the processor.
5. The face mask of claim 2, further comprising a motion detection sensor communicatively coupled to the processer configured to detect a plurality of motion activity data within a predefined proximity of the mask body.
6. The face mask of claim 2, wherein the pulsing laser element is a gamma radiation detection mechanism communicatively coupled to the processor comprising a scintillator wherein the scintillator is configured to emit a plurality of low-energy photons.
7. The face mask of claim 1, further comprising a polyurethane layer allocated along an exterior surface of the mask body; and
    a plurality of breathing valves, wherein the ultraviolet light element is integrated along a first exterior surface associated with a first breathing valve and the pulsing laser element is integrated along a second exterior surface associated with a second breathing valve.
8. The face mask of claim 2, further comprising a short-range wireless communication mechanism configured to communicate with the processor to generate a personal area network (PAN).
9. The face mask of claim 1, further comprising a ventilation mechanism comprising a plurality of fans coupled to a ventilation power source wherein the ventilation mechanism is configured to be integrated into the mask body and generate an airflow away from the mask body.

\* \* \* \* \*